(12) United States Patent
Scopton

(10) Patent No.: US 6,997,899 B2
(45) Date of Patent: Feb. 14, 2006

(54) RAPID EXCHANGE DILATION CATHETER FOR NON-VASCULAR APPLICATIONS

(75) Inventor: Paul M. Scopton, Winchester, MA (US)

(73) Assignee: Boston Scientific Scimed, Inc,, Maple Grove, MN (US)

( * ) Notice: Subject to any disclaimer, the term of this patent is extended or adjusted under 35 U.S.C. 154(b) by 0 days.

(21) Appl. No.: 10/321,910

(22) Filed: Dec. 17, 2002

(65) Prior Publication Data

US 2004/0116852 A1    Jun. 17, 2004

(51) Int. Cl.
*A61M 29/00*    (2006.01)

(52) U.S. Cl. ................................. 604/103.04

(58) Field of Classification Search ............ 604/96.01, 604/103.04, 102.01, 102.02, 102.03, 523, 604/525, 104.09, 510, 524; 606/191–193
See application file for complete search history.

(56) References Cited

U.S. PATENT DOCUMENTS

| | | | | |
|---|---|---|---|---|
| 4,894,057 A | * | 1/1990 | Howes ..................... 604/523 |
| 5,061,273 A | * | 10/1991 | Yock ....................... 606/194 |
| 5,387,226 A | | 2/1995 | Miraki |
| 5,389,087 A | * | 2/1995 | Miraki ..................... 604/247 |
| 5,410,797 A | * | 5/1995 | Steinke et al. ............ 29/435 |
| 5,413,557 A | * | 5/1995 | Solar ..................... 604/103.1 |
| 5,484,449 A | * | 1/1996 | Amundson et al. ........ 606/108 |
| 5,516,336 A | * | 5/1996 | McInnes et al. .......... 606/194 |
| 5,609,574 A | * | 3/1997 | Kaplan et al. ............ 604/508 |
| 5,634,902 A | * | 6/1997 | Johnson et al. ......... 604/96.01 |
| 5,782,740 A | * | 7/1998 | Schneiderman ............ 600/1 |
| 5,833,650 A | * | 11/1998 | Imran ..................... 604/509 |
| 6,027,475 A | | 2/2000 | Sirhan et al. |
| 6,142,926 A | * | 11/2000 | Schneiderman ............ 600/3 |
| 6,458,099 B1 | * | 10/2002 | Dutta et al. ............ 604/103.04 |
| 6,548,010 B1 | * | 4/2003 | Stivland et al. ........... 264/482 |
| 6,589,207 B1 | * | 7/2003 | El-Nounou ........... 604/103.04 |
| 6,663,648 B1 | * | 12/2003 | Trotta ..................... 606/194 |
| 6,733,473 B1 | * | 5/2004 | Reifart et al. ........... 604/96.01 |

FOREIGN PATENT DOCUMENTS

| | | |
|---|---|---|
| EP | 1163925 | 12/2001 |
| WO | WO 92/17236 | 10/1992 |

* cited by examiner

*Primary Examiner*—Manual Mendez
(74) *Attorney, Agent, or Firm*—Fay Kaplun & Marcin, LLP

(57) ABSTRACT

A flexible catheter for insertion into a body lumen, comprises a guide wire lumen extending from a distal port at a distal end of the catheter to a proximal port separated from a proximal end of the catheter and a stiffening member extending from the proximal port to a proximal end of the catheter.

11 Claims, 1 Drawing Sheet

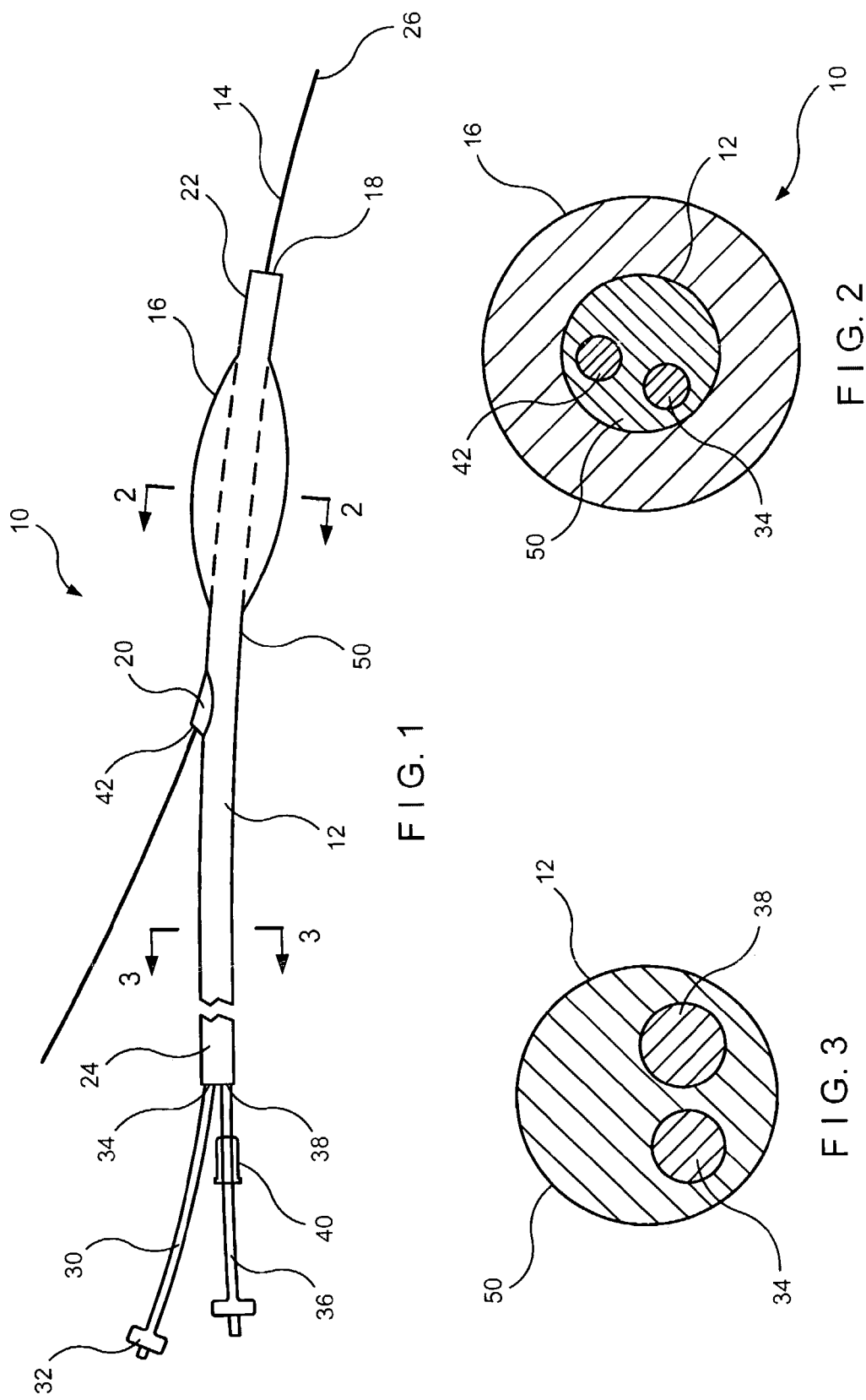

RAPID EXCHANGE DILATION CATHETER FOR NON-VASCULAR APPLICATIONS

FIELD OF THE INVENTION

The present invention is applicable to the field of catheters, and in particular to the field of balloon catheters used for dilation of body cavities.

BACKGROUND OF THE INVENTION

Endoscopic procedures for treating abnormal pathologies within various body cavities, such as, for example, the alimentary canal, the biliary tree and the pulmonary system are increasing in number. In these procedures, an endoscope may provide access to the general area of a desired cavity or duct using direct visualization. However, smaller ducts may require navigation using a only a catheter in conjunction with fluoroscopy and guide wires.

In many cases, treatment of the areas within such small diameter ducts requires use of more than one catheter, necessitating a catheter exchange during the procedure. These catheters may, for example, be specialized for the delivery of contrast media for fluoroscopic visualization of the anatomical details of the duct, to deliver therapeutic agents, or to perform a dilation of the duct. In the latter case, the catheter may include an expandable portion that mechanically dilates the duct when expanded. A catheter exchange typically involves removing the first catheter from the endoscope, over the guide wire, and advancing a second catheter over the guide wire to the desired treatment site. Once the guide wire is in place relative to the targeted area, it is highly desirable to maintain the position of the guide wire during subsequent catheter procedures, including during catheter exchanges, to facilitate positioning subsequently utilized catheters or other devices at the target area. If the guide wire's positioning at the target area is lost during such a procedure, re-directing the guide wire through the body ducts to the target site may be difficult and time consuming.

To maintain the position of the guide wire, a physician typically grasps the proximal end of the guide wire and/or catheter with one hand while performing the corresponding exchange with the other. For certain procedures, the length of the standard guide wire may be insufficient to allow a physician to maintain his grasp of the catheter as the full length of the catheter is removed thereover. To alleviate this difficulty, additional devices such as guide wire extenders may be used. However, utilizing such additional devices adds to the complexity of and time required for the exchange. In addition, the extended length of the guide wire (up to two meters or more) may require a second operator to assist in handling the apparatus during the procedure.

SUMMARY OF THE INVENTION

The present invention is directed to a flexible catheter for insertion into a body lumen, comprising a guide wire lumen extending from a distal port at a distal end of the catheter to a proximal port separated from a proximal end of the catheter and a stiffening member extending from the proximal port to a proximal end of the catheter.

The present invention is further directed to a method of treating tissue at a target location within a body lumen, comprising the steps of inserting a guide wire through the body lumen to the target location, inserting a proximal end of the guide wire into a distal port of a guide wire lumen of a catheter and sliding the catheter therealong until the guide wire exits a proximal port thereof, the proximal port of the guide wire being spaced from a proximal end of the catheter and, wherein the catheter includes a stiffening member extending from the proximal end thereof to a location adjacent to the proximal port of the guide wire lumen in combination with the steps of sliding the catheter along the guide wire to the target location and treating tissue at the target location using the catheter.

BRIEF DESCRIPTION OF THE DRAWINGS

FIG. 1 is a side view showing an embodiment of the rapid exchange balloon catheter according to the present invention;

FIG. 2 is a cross sectional view on line II—II of the rapid exchange catheter shown in FIG. 1; and FIG. 3 is a cross sectional view on line III—III of the rapid exchange catheter shown in FIG. 1.

DETAILED DESCRIPTION

The present invention may be further understood with reference to the following description and the appended drawings, wherein like elements are referred to with the same reference numerals. According to embodiments of the present invention, a rapid exchange catheter is utilized to dilate any of various body cavities, and in particular non-vascular body cavities such as gastrointestinal passages, biliary, hepatic and pancreatic ducts, pulmonary passages and the like. However, those skilled in the art will understand that the catheter according to the present invention may be employed in any body lumen which a physician wishes to dilate. As described below, the catheter may include lumens adapted for any or all of the various functions described herein as well as lumens for any other known purpose.

Embodiments according to the present invention facilitate the insertion of the catheter over a guide wire, and simplify exchanges of catheters without disturbing a positioning of the guide wire at a target location. As described in more detail below, embodiments of the present invention allow shorter guide wires to be utilized while maintaining the ability of a physician to maintain a secure grip on the wire during exchange procedures.

A typical procedure using a catheter in a small, non-vascular target passage or duct, may begin with the insertion of an endoscope or a bronchoscope to visualize the larger body cavities leading to the target passage. For target areas located within small diameter ducts, the endoscope's large size may make it impossible to directly access the target area with the endoscope. Therefore, these ducts must be accessed by extending a catheter and guide wire combination distally from the endoscope through the small diameter ducts to the target area. The guide wire is often inserted first under, for example, fluoroscopic guidance or another method known in the art. The guide wire may be extended from within a lumen of the endoscope, or may be inserted separately, alongside the endoscope. The guide wire may thus be viewed both through the endoscope, and using fluoroscopy. Once the distal end of the guide wire has reached the target area, it is important to maintain it in place. If the position is lost, the guide wire must be guided again into position, significantly adding to the time required to complete the procedure.

Once the guide wire is in place, a catheter may be extended, for example from within a lumen of the endoscope, along the guide wire to the target location. For example, the catheter may include a guide wire lumen through which the guide wire passes. The catheter may, for example, be "threaded" onto the guide wire, so that the guide wire enters the guide wire lumen near a distal tip of the catheter, follows it along a portion of the length thereof, and exits at a more proximal location along the catheter. The guide wire is free to slide longitudinally within the guide wire lumen of the catheter, but is constrained radially by the walls of the guide wire lumen. In addition to guiding the catheter, the guide wire also provides a certain amount of stiffness to the catheter, so that it will not buckle as readily as it might without a guide wire received therein.

FIG. 1 shows an exemplary embodiment of a rapid exchange dilation catheter 10 according to the present invention. As described above, as would be understood by those of skill in the art, the dilation catheter 10 may be extended into the body from an endoscope or from a bronchoscope (not shown in the drawings), or may be inserted directly into a body cavity, depending on the application. The dilation catheter 10 extends from a distal end 22 and a proximal end 24. The distal end 22 is adapted to be inserted inside a body lumen via, for example, a natural body orifice or a surgical opening while the proximal end 24 typically remains outside of the body cavity throughout the procedure, and may, for example, include a handle, the various actuators or controls and connections necessary to operate the catheter 10. As would be understood by those of skill in the art, the catheter 10 is preferably a flexible, multi-lumen catheter, so that it is able to follow the guide wire through narrow body cavities and ducts. Those of skill in the art will appreciate that different structural constructions of the catheter may be employed, while remaining within the scope of the present invention.

As shown in FIGS. 1–3, the catheter 10 may include an expandable element, for dilating the lumen at the area to be treated. For example, the expandable element may include a balloon portion 16 formed near the distal end 22, so that, when inflated, the balloon portion 16 expands a diameter of the lumen adjacent to the target location in the duct pinpointed by the distal end 26 of guide wire 14. In this manner, the balloon portion 16 may be accurately moved to the target location by moving the catheter 10 along the guide wire 14. As would be understood by those of skill in the art, the balloon portion 16 may be coupled to a source of inflation fluid via an inflation lumen 34 which may be connected to a fluid supply tube 30 at one end, and to the balloon portion 16 at the other end. A valve or other control device 32 may be used to selectively introduce or remove the inflation fluid, and cause the balloon portion 16 to expand or collapse. As would be understood by those of skill in the art, the inflation fluid may comprise air, saline or other suitable fluid.

As described above, a guide wire 14 may be used according to the invention to precisely locate the distal end 22 of catheter 10 at the target area. As described above, the guide wire 14 is inserted into a body cavity or duct to be treated, and the distal end 26 thereof is maneuvered to a position adjacent to the target area. The proximal end of the guide wire 14 is then inserted into the guide wire lumen 42 of the catheter 10 and the catheter 10 is pushed along the guide wire 14 until the distal end 22 of the catheter 10 is also adjacent to the target area. According to the exemplary embodiment shown, the guide wire lumen 42 extends from a distal port 18 to a proximal port 20, and passes below balloon portion 16, as shown in FIG. 2. The guide wire 14 is inserted into the guide wire lumen 42 via a distal port 18 and is slid therethrough under the balloon portion 16 and out of a proximal port 20. The distal port 18 may, for example, be formed at the distal end 22, so that the guide wire 14 exits therefrom substantially along an axis of the catheter 10. The proximal port 20 may, for example, be formed on a side surface of the catheter 10 spaced from a proximal end thereof so that the guide wire 14 exits at an angle therefrom and does not pass through a proximal part of catheter 10.

As described above, conventional over the wire catheters often require a guide wire that is more than twice the length of the catheter, as the guide wire is threaded through the entire length of the catheter. The length of the guide wire makes it difficult to handle the apparatus, especially if the catheter is to be replaced while maintaining the guide wire in place. According to embodiments of the present invention, the guide wire 14 may be much shorter, since it only has to extend through the part of catheter 10 between the distal port 18 and the proximal port 20 and does not extend through that portion of the catheter 10 which is proximal of the proximal port 20. The distance between the distal port 18 and the proximal port 20 is preferably significantly shorter than the total length of catheter 10, so that the guide wire 14 does not need to be longer than the catheter 10 to function properly. For example, in a catheter 10 having a length of 100 cm, the proximal port 20 of the guide wire lumen 42 may be located approximately 10 cm from a proximal end of the balloon portion 16. Those skilled in the art will understand that the distance from the proximal end of the balloon from the distal port 18 will vary depending on the length of the balloon employed as the balloon portion 16. The balloon will generally be between 2 cm and 10 cm in length. The length of the guide wire lumen 42, between ports 18 and 20, is kept to a minimum length which allows guidance of the distal end 22 and of the balloon portion 16 into the target area. In a preferred embodiment, the catheter 10 is threaded over the guide wire 14 at least within the portion containing the dilation mechanism, e.g., the balloon portion 16, which must be accurately placed with respect to the target area. In one exemplary embodiment, the guide wire lumen may preferably have a length of approximately 10-15 cm.

Catheters 10 according to the invention are especially beneficial in situations where a first catheter 10 must be removed from the guide wire 14 so that a second catheter, which may be of any construction, may be replaced thereon and guided to the target area. As described above, as only a small portion of the guide wire 14 is contained within the guide wire lumen 42, the operator may maintain hands-on control of the guide wire 14 at all times during removal of the first catheter 10 from the body. That is, since the majority of the length of the guide wire 14 is outside the catheter 10 and accessible, the operator may grasp the guide wire 14 near the point where it enters the body cavity to manually prevent it from moving out of place as the catheter 10 is retracted. When the proximal port 20 exits the body, the operator may grasp a more proximal portion of the guide wire 14 until the distal port 18 exits the body. At this point, the operator may grasp the portion of the guide wire 14 extending from the distal port 18 into the body while completely removing the catheter 10 from the guide wire 14. Thereafter, the proximal end of the guide wire 14 may be inserted into the second catheter in the standard manner and the second catheter may be advanced along the guide wire 14 to the target area. In this manner, the operator may maintain a grasp on the guide wire 14 at all times to maintain its position at the target area.

After the first catheter 10 has been removed, a second catheter may then be advanced to the target area by inserting the guide wire 14 into a guide wire lumen thereof and sliding the second catheter along the guide wire 14 to the target area.

If the second catheter is also formed as a catheter 10 in accord with the present invention, the guide wire 14 will be inserted into the distal opening 18 and drawn out of the proximal port 20 and inserted into the body cavity while grasping the proximal portion of the guide wire 14 to maintain it at its location adjacent the target area. Thus, the entire operation may be performed by one unassisted operator.

The catheter 10 may also include a stiffening member 36 that extends distally from proximal end 24 of the catheter 10 along a portion of the length thereof. The stiffening member 36 increases the longitudinal strength and rigidity of the catheter 10 to facilitate insertion of the device into body lumens. In particular, the stiffening member 36 stiffens the proximal portion of catheter 10 where guide wire 14 is external to catheter 10 (i.e., the portion of the catheter 10 proximal of the proximal port 20). Thus, the stiffness of the catheter 10 is maintained along its length despite the fact that a guide wire 14 is not present through the proximal portion thereof. In one exemplary embodiment according to the present invention, the stiffening member 36 extends from the proximal end 24 to a location proximate to the balloon portion 16. However, those skilled in the art will understand that the stiffening member 36 may extend distally beyond the past the proximal port 20 to enhance the stiffness of the distal part of the catheter 10. In one specific exemplary embodiment, the stiffening member 36 fits within a second lumen of the catheter 10, such as stiffening member lumen 38, which may extend from the proximal end 24 to a proximal end of the balloon portion 16. More preferably, the stiffening member 36 will extend from the proximal end 24 to the proximal port 20 so that the stiffness of the catheter 10 with a guide wire 14 received therein is substantially constant along its length. The guide wire 14 imparts to the portion of the catheter 10 extending distally of the proximal port 20 an additional stiffness substantially equal to that imparted to the proximal portion of the catheter by the stiffening member 36 so that the column strength of the entire catheter 10 is sufficient to enable it to be pushed through the body lumen to the target area.

The stiffening member 36 may be adapted to fit into any of the lumens of the catheter 10 to facilitate manipulation of catheter 10 by the operator. For example, a handle portion may be provided at the proximal end of the stiffening member 36 to facilitate grasping the device. The rigidity of the stiffening member 36 is preferably selected such that, once it is has been inserted into the lumen 38, the catheter 10 remains sufficiently flexible to follow the curvature of the duct or cavity being treated, but at the same time has column stiffness required to allow it to be pushed through the body lumen to the target area. The stiffening member 36 may optionally be removable from the catheter 10. In one embodiment, as shown in FIG. 1, a lock 40 may be used to secure the stiffening member 36 in place relative to the proximal end 24. As would be understood, when in an open configuration, the lock 40 permits removal of the stiffening member 36 from the lumen 38 while, when in the closed position, the lock 40 prevents removal of the stiffening member 36 therefrom.

The catheter 10 may be provided with additional lumens used to carry out various functions. For example, certain procedures may require injection of a contrast media to the target area to assist in fluoroscopic visualization of the region being treated. Alternatively, a procedure may require injection of a therapeutic agent to treat the target area. Thus, the catheter 10 may include an injection lumen with an exit port distal of the balloon portion 16. The catheter 10 may include separate injection lumens for contrast media and therapeutic agents or these fluids may be applied via a single multi use lumen of the catheter 10. In one exemplary embodiment, the lumen 38 may be used to carry the various agents, as well as to hold stiffening member 36. In that case, the lumen 38 will extend all the way to the distal end 22 of catheter 10, while only a proximal portion thereof is occupied by the stiffening member 36. In other embodiments, the stiffening member 36 may utilize a separate lumen of the catheter 10, or may be secured to the catheter 10 without the use of a lumen, for example by being integrated into or attached to a surface of a lumen the catheter 10.

The catheter 10 according to the present invention includes an opening (i. e. port 20) near balloon portion 16 through which the guide wire 14 may enter and/or exit the guide wire lumen 42. Care must be taken to prevent fluids from entering the catheter 10 and/or leaking from the catheter 10 at this location. A sheath 50 may be placed over the distal portion of catheter 10 to prevent leaks during injection of fluids through the various lumens of the catheter 10. In one embodiment, the sheath 50 may extend distally from a point proximal of the proximal port 20 a predetermined distance past the proximal port 20. The sheath 50 may, for example, be between 0–30 cm in length. In this manner the proximal port 20 is sealed by the sheath 50, and any leaks that may form at the exit of the guide wire 14 are contained therewithin. At the same time, bodily fluids and contaminants are prevented from entering the catheter 10. For example, the sheath 50 may be made of a polymeric material that is heat-shrunk over catheter 10.

A catheter 10 according to the present invention may, for example, be used to dilate a pulmonary bronchial tube. The procedure may begin by inserting a bronchoscope near the target region and extending a guide wire 14 distally therefrom. Alternatively, the guide wire 14 may be inserted separately from the bronchoscope. The bronchoscope is then used only for visual guidance of items to the point within the body lumens where the diameter is reduced to a level insufficient to accommodate the bronchoscope. The guide wire 14 is then extended from the bronchoscope and moved into the selected bronchial tube until its distal end 26 reaches the target area, as ascertained using, for example, fluoroscopy. From this point on, the distal end 26 of the guide wire 14 should not be disturbed from its position near the target area to be treated.

The proximal end of the guide wire 14 is then inserted into the distal port 18 of the guide wire lumen 42 and the catheter 10 is slid along the guide wire 14 until the guide wire 14 exits from the proximal port 20. During the insertion of the guide wire 14 into the catheter 10, as described above, the operator grasps the portion of the guide wire extending distally from the catheter 10 to maintain the position of the guide wire 14 relative to the target area. Once the guide wire 14 has exited from the proximal port 20, the operator grasps this proximal part of the guide wire 14 and slides the catheter 10 along the guide wire into the body lumen until a distal end 22 thereof reaches the target area. This procedure may be carried out by one operator unassisted, since it is easy to maintain control of the shorter guide wire with one hand, leaving the other hand free.

Once catheter 10 is in place, an inflation fluid may be introduced to expand the balloon portion 16. The bronchial tube is thus dilated, and therapeutic agents may be introduced through catheter 10 to further treat the bronchial tube. If catheter 14 is to be replaced by a second catheter, the operator may simply hold in place the exposed portion of guide wire 14 with one hand, and pull out the catheter 10 with the other hand until the distal port 18 exits the body. At this point, the operator grasps the portion of the guide wire 14 extending distally from the distal port 18 and completely removes the catheter 10 from the guide wire 14. Thereafter, any desired catheter may be coupled to the guide wire 14 and advanced to the target area. Exchanging the catheter may be required, for example, in the case of failure of the first balloon to deploy, or if closer inspection of the target site reveals the need for a different surgical tool to treat the cavity, etc.

In the preceding specification, the present invention has been described with reference to specific exemplary embodiments thereof. It will, however, be evident that various modifications and changes may be made thereto without departing from the broadest spirit and scope of the present invention as set forth in the claims that follow. The specification and drawings are accordingly to be regarded in an illustrative rather than restrictive sense.

What is claimed is:

1. A flexible catheter for insertion into a body lumen, comprising:
    a guide wire lumen extending from a distal port at a distal end of the catheter to a proximal port separated from a proximal end of the catheter;
    a stiffening member lumen separate from the guide wire lumen, the stiffening member lumen extending from the proximal end of the catheter to an opening at the distal end of the catheter so that fluid supplied thereto is delivered to an area of the body lumen adjacent to the distal end of the catheter; and
    a stiffening member extending within the stiffening member lumen from the proximal end of the catheter to a point adjacent to the proximal port.

2. The flexible catheter according to claim 1, further comprising an expandable element mounted adjacent to the distal end of the catheter for dilating a lumen in which the catheter is inserted.

3. The flexible catheter according to claim 2, wherein the expandable element includes an inflatable structure coupled to an inflation fluid lumen.

4. The flexible catheter according to claim 1, wherein the expandable element is mounted between the proximal and distal ports of the guide wire lumen.

5. The flexible catheter according to claim 1, further comprising a stiffening member locking mechanism to lock the stiffening member within the stiffening member lumen.

6. The flexible catheter according to claim 1, wherein the proximal port is a lateral port formed on a side surface of the flexible catheter.

7. The flexible catheter according to claim 1, further comprising a sheath encasing a portion of the flexible catheter including the proximal port.

8. The flexible catheter according to claim 7, wherein the sheath is formed of an impermeable material.

9. The flexible catheter according to claim 1, wherein the inflatable structure includes a balloon which expands radially from the flexible catheter when inflated.

10. A method of treating tissue at a target location within a body lumen, comprising the steps of:
    inserting a guide wire through the body lumen to the target location;
    inserting a proximal end of the guide wire into a distal port of a guide wire lumen of a catheter and sliding the catheter therealong until the guide wire exits a proximal port thereof, the proximal port of the guide wire lumen being spaced from a proximal end of the catheter;
    sliding the catheter along the guide wire to the target location;
    inserting a stiffening member into a stiffening member lumen until the stiffening member extends between a proximal end of the catheter and a point substantially equally distal thereof with the proximal port, the stiffening member lumen separate from the guide wire lumen and extending from the proximal end of the catheter to an opening formed in a distal end thereof; and
    treating tissue at the target location using the catheter.

11. The method according to claim 10, further comprising removing the catheter from the body cavity by sliding said catheter along the guide wire, and threading a second catheter onto the guide wire to guide the second catheter to the target location.

* * * * *